United States Patent [19]
Ezaki et al.

[11] 4,283,389
[45] Aug. 11, 1981

[54] NOVEL ANTIBIOTIC, BN-183B SUBSTANCE

[75] Inventors: Norio Ezaki; Shinji Miyadoh; Yasuaki Ogawa; Takashi Hisamatsu, all of Yokohama; Harumi Fukuyashu, Yokosuka; Yujiro Yamada, Yokohama, all of Japan

[73] Assignee: Meiji Seika Kaisha Ltd., Tokyo, Japan

[21] Appl. No.: 105,442

[22] Filed: Dec. 19, 1979

[30] Foreign Application Priority Data

Dec. 27, 1978 [JP] Japan .................................. 53-159820

[51] Int. Cl.$^3$ .............................................. A61K 35/00
[52] U.S. Cl. ..................................... 424/116; 435/170
[58] Field of Search ......................... 424/116; 435/170

[56] References Cited
PUBLICATIONS

Chemical Abstracts 88:20527x (1978).

*Primary Examiner*—Jerome D. Goldberg
*Attorney, Agent, or Firm*—Sughrue, Rothwell, Mion, Zinn and Macpeak

[57] ABSTRACT

A novel antibiotic designated BN-183B substance is disclosed which is produced by cultivating a strain of the genus Pseudomonas. The antibiotic has a strong action against Gram-positive and Gram-negative bacteria.

2 Claims, 2 Drawing Figures

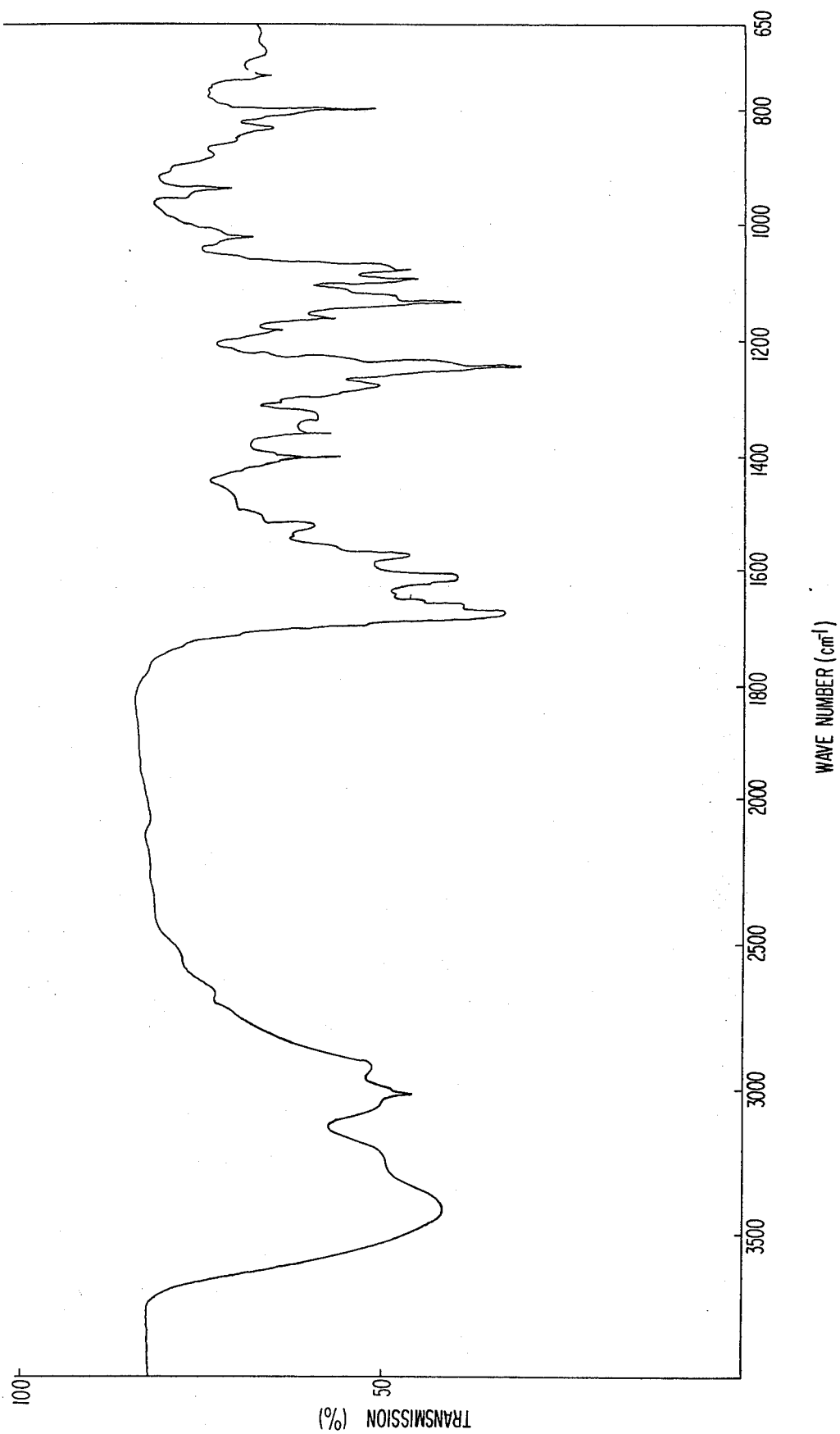

NOVEL ANTIBIOTIC, BN-183B SUBSTANCE

BACKGROUND OF THE INVENTION

This invention relates to a novel antibiotic and to a process for production thereof. More specifically, this invention relates to a novel antibiotic BN-183B substance which exists in the cultivated product of a specified strain of the genus Pseudomonas, which shows a strong growth inhibiting action on Gram-positive and Gram-negative bacteria and anticancerous and antiviral activities; and to a process for producing the antibiotic.

SUMMARY OF THE INVENTION

According to this invention, there is provided a novel antibiotic, BN-183B substance, whose hydrochloride has the following characteristics:

(1) Elemental analysis values: C 39.84%, H 5.25%, N 6.43%, Cl 22.90%.

(2) Molecular weight: 383.

(3) Molecular formula: $C_{14}H_{20}N_2O_6Cl_2 \cdot HCl$.

(4) Melting point: begins to turn brownish at 190° C. and to foam and decompose at 214° C.

(5) Ultraviolet absorption spectrum: shown in FIG. 1.

(6) Infrared absorption spectrum: absorption bands at 3400, 3020, 1680, 1620, 1570, 1520, 1400, 1360, 1330, 1270, 1240, 1180, 1160, 1130, 1090, 1080, 1020, 930, 880, 850, 830, 800, 740, 700 cm$^{-1}$ and absorption spectrum as shown in FIG. 2.

(7) Specific rotation: $[\alpha]_D^{23}$ $-9°$ (c=1, water).

(8) Solubility: very soluble in water, slightly soluble in methanol, and scarcely soluble in acetone, chloroform and ethyl acetate.

(9) Color reactions:
Positive: ferric chloride, ninhydrin and Fehling
Negative: Molisch and biuret

(10) Distinction by neutrality, acidity and basicity: behaves as a basic substance in filter paper electrophoresis.

(11) Appearance: white or slightly yellowish powder

(12) Rf values in thin-layer chromatography:
Butanol-acetic acid-water (2:1:1): 0.66
Ethyl acetate-acetic acid-water (60:17:17): 0.34
Butanol-pyridine-acetic acid-water (6:4:1:3): 0.65.

The invention also provides a process for producing BN-183B substance by cultivating a BN-183B substance-producing strain of the genus Pseudomonas and separating and recovering the BN-183B substance from the culture broth.

BRIEF DESCRIPTION OF THE ACCOMPANYING DRAWINGS

FIG. 1 shows the ultraviolet absorption spectrum of the hydrochloride of BN-183B substance, the measurement being made in a concentration of 10 mcg/ml in distilled water (I), 0.1 N sulfuric acid (II) and 0.1 N NaOH (III); and FIG. 2 is an infrared absorption spectrum of the hydrochloride of BN-183B substance measured by the KBr tablet method.

DETAILED DESCRIPTION OF THE INVENTION

Figure 1:
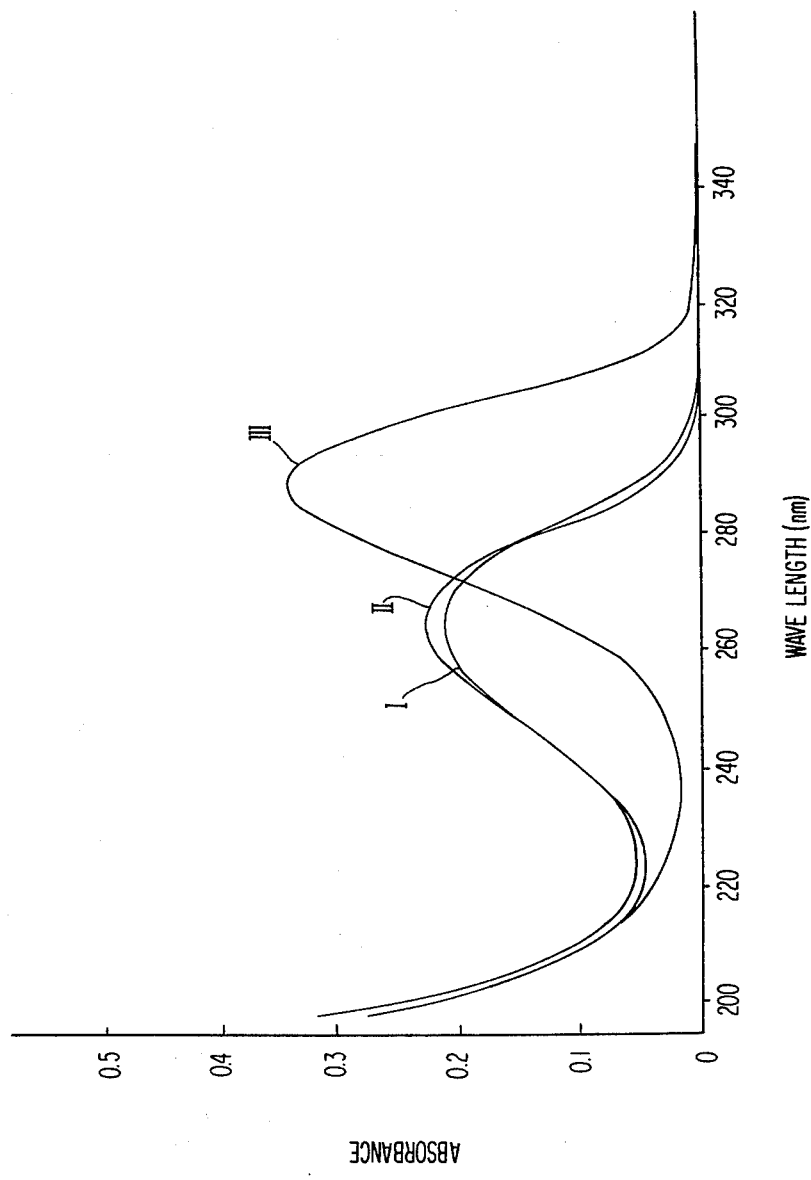

One example of a BN-183B substance-producing strain used in this invention is Pseudomonas sp. BN-183 strain (BN-183 strain) isolated from the soil in Tokaimura, Ibaragi Prefecture, Japan. The BN-183 strain is deposited in Fermentation Research Institute, Agency of Industrial Science and Technology, Ministry of International Trade and Industry of Japan under the accession number FERM-P No. 3332 and in the American Type Culture Collection (ATCC) under ATCC number 31571 (deposited on Sept. 26, 1979).

The bacteriological properties of the BN-183 strain are described as follows in Japanese Patent Application (OPI) No. 105292/77 (published on Sept. 3, 1977) (The term "OPI" as used herein refers to a "published unexamined Japanese patent application").

(A) Morphological characteristics

The cells cultivated on a bouillon-agar medium are rod-shaped, 0.5–0.7×0.7–2.0 microns in size, and movement with polar flagella is observed. No formation of spores nor exhibition of polymorphism. Gram stain is negative.

(B) Cultural characteristics (1) Bouillon-agar medium:
The pale brown cells proliferate. The colonies do not show marked wrinkled growth, viscousness and motility. No formation of diffusible pigments.

(2) Bouillon medium:
The entire medium is turbid and a thin pellicle is formed on the liquid surface.

(3) Bouillon-gelatin stab culture medium:
Liquefied.

(4) Litmus milk culture:
Completely liquefied on cultivation at 28° C. for 2 weeks to show weak alkalinity.

(C) Physiological characteristics (1) Reduction of nitrate: negative
(2) Denitration reaction: negative
(3) MR test: positive
(4) VP test: negative
(5) Formation of indole: negative
(6) Formation of hydrogen sulfide: negative by the lead paper method.
(7) Hydrolysis of starch: positive
(8) Utilization of citric acid: positive by the Simmons and Christensen method.
(9) Utilization of inorganic nitrogen sources:
An ammonium salt can be utilized as the only N source.
(10) Formation of pigments: No marked formation of pigments is noted in King A and B media.
(11) Oxidase: positive
(12) Cannot grow below 5° C. and above 41° C.
(13) No requirement for vitamins or amino acids.
(14) OF test (Heuleifson's method) O type
(15) No growth under anaerobic conditions
(16) Utilization of carbon sources:
Glucose, maltose, xylose, lactose, D-arabinose, Cellobiose, L-threonine, L-ornithine, and saccharate.

The BN-183 strain having the above bacteriological properties was compared with strains described in Bergey's Manual of Determinative Bacteriology, 8th Edition (1974), and the following conclusions were drawn.

1. This strain belongs to the genus Pseudomonas because it is a Gram-negative rod-shaped bacterium which does not form spores, moves with polar flagella, and is absolutely aerobic.

2. From its characteristic ability to utilize a broad range of carbon sources, this strain is judged to be akin to *Pseudomonas cepacia*.

Various culture media used in ordinary microbial fermentation processes can be used to cultivate BN-183B substance-producing strains and to produce and accumulate the BN-183B substance. Glucose, glycerol, dextrin, and millet jelly, for example, can be used as carbon sources. Nitrogen sources that can be used include, for example, peptone, meat extract, bouillon powder, corn steep liquor, soybean cake, ammonium sulfate, and ammonium chloride. Inorganic salts such as sodium chloride and calcium carbonate are additionally used whenever required. If desired, an anti-foamer can be added.

The cultivation can be suitably conducted using a liquid culture medium, such as a shake-culture method, or an aeration agitation culture method. The cultivation temperature is optimal in the range of about 20° to about 35° C., and a suitable cultivation time ranges from 1 to 3 days.

The BN-183B substance is mainly accumulated extracellularly in the cultivation liquid.

In assaying the BN-183B substance, its anti-bacterial activity is utilized and *Bacillus subtilis* ATCC 6633 is used as an assaying strain. A mixture of 2% of mycin assay agar (a product of Kyoei Seiyaku K.K.) and 0.5% of bacto-agar (a product of Difco) is used as an assaying culture medium. When BN-183B substance (pure product) is assayed under the above conditions, the relation between the logarithm of the concentration within the range of 20 to 500 mcg/ml and the diameter of the inhibitory zone is linear, and an inhibitory zone having a diameter of 16 to 29 mm is given corresponding to the above concentration range (paper disc method).

The BN-183B substance can be extracted and purified according to its physical and chemical properties described below. The method shown below is efficient. That is, the fermentation broth containing the active ingredient is filtered to remove solid matter. To the filtrate is added an adsorbent such as an activated carbon (for example, an activated carbon for chromatographic use (a product of Wako Purechemical Industries Ltd.)) or a high porous resin (for example, Diaion HP-20 (a trade name, a product of Mitsubishi Chemical Industries Ltd., Japan)) followed by stirring and, thus, the active substance is adsorbed on the adsorbent. Then, the active substance is eluted with an aqueous acetone solution or aqueous methanol solution and the solution is concentrated to dryness to obtain a crude BN-183B substance. The crude product is then purified by a suitable combination of a column chromatography using CM Sephadex C-25 (a product of Pharmacia Co., Sweden), a gel-filtration, a column chromatography using ion-exchange resins to obtain white powder of the BN-183B substance. A separation between the BN-183B substance of the present invention and the BN-183 substance of Japanese Patent Application (OPI) No. 105292/77 can be carried out, for example, by a thin-layer chromatography using silica gel and ethyl acetate-acetic acid-water (60:17:17 by volume) as a developing solvent. The BN-183B substance of the present invention can be obtained by collecting fractions having an Rf value of 0.34 in the above thin-layer chromatography and the BN-183 substance of Japanese Patent Application (OPI) No. 105292/77 can be obtained by collecting fractions having an Rf value of 0.55 in the above thin-layer chromatography and, thus, the BN-183B substance of the present invention can be separated from the BN-183 substance of Japanese Patent Application (OPI) No. 105292/77.

When the resulting powder product is chromatographed on a thin layer of silica gel using various solvent systems, e.g., butanol-acetic acid-water, ethyl acetate-acetic acid-water, butanol-pyridine-acetic acid-water, etc., a single spot is formed in all systems used. This shows that the resulting powder product is BN-183B substance in pure form.

The physicochemical characteristics of the BN-183B substance, as the hydrochloride, are as follows:

(1) Elemental analysis: C 39.84%, H 5.25%, N 6.43%, Cl 22.90%.

(2) Molecular weight: 383.

(3) Molecular formula: $C_{14}H_{20}N_2O_6Cl_2 \cdot HCl$.

(4) Melting point: It begins to turn brownish at 190° C. and to foam and decompose at 214° C.

(5) Ultraviolet absorption spectrum: As shown in FIG. 1.

(6) Infrared absorption spectrum: Absorption bands at 3400, 3020, 1680, 1620, 1570, 1520, 1400, 1360, 1330, 1270, 1240, 1180, 1160, 1130, 1090, 1080, 1020, 930, 880, 850, 830, 800, 740, 700 cm$^{-1}$ and absorption spectrum as shown in FIG. 2.

(7) Specific rotation: $[\alpha]_D^{23}$ $-9°$ (c=1, water).

(8) Solubility: Very soluble in water, slightly soluble in methanol, and scarcely soluble in acetone, chloroform and ethyl acetate.

(9) Color reactions:
Positive: ferric chloride, ninhydrin and Fehling
Negative: Molisch and biuret

(10) Distinction by neutrality, acidity or basicity: It shows a behavior as a basic substance in filter paper electrophoresis.

(11) Appearance: white to slightly yellowish powder

(12) Rf values in thin-layer chromatography:
Butanol-acetic acid-water (2:1:1): 0.66
Ethyl acetate-acetic acid-water (60:17:17): 0.34
Butanol-pyridine-acetic acid-water (6:4:1:3): 0.65

Table 1 below summarizes the minimum growth inhibitory concentrations of the BN-183B substance on various microorganisms. It shows a strong inhibitory activity on Gram-positive and Gram-negative bacteria, and is useful in medicines, veterinary medicines and disinfectants.

TABLE 1

| Microorganisms | Minimum Growth Inhibitory Concentration (mcg/ml) |
|---|---|
| *Staphylococcus aureus* 209P JC-1 | 0.20 |
| *Staphylococcus aureus* Smith S-424 | 0.20 |
| *Staphylococcus epidermidis* ATCC14990 | 0.20 |
| *Staphylococcus faecalis* ATCC8043 | 0.39 |
| *Escherichia coli* NIHJ JC-2 | 1.56 |
| *Escherichia coli* K-12 IAM 1264 | 0.78 |
| *Proteus vulgaris* OX19 | 6.25 |

The culture media used were a nutrient agar (a product of Difco).

The LD$_{50}$ values of the present substance in mice are shown in Table 2.

TABLE 2

| Administration Route | LD$_{50}$ (mg/kg) |
|---|---|
| Oral | 50 |
| Intravenous | 4.1 |
| Intramuscular | 4.1 |
| Intraperitoneal | 4.3 |
| Subcutaneous | 6.0 |

The BN-183B substance also shows anticancerous activity, and a composition containing this substance is an effective anti-cancer agent. Lymphocytic leukemia P-388 or lymphoid leukemia L-1210 cells were transplanted intraperitoneally in an amount of $1\times10^6$ per mouse into $CDF_1$ mice or $BDF_1$ mice (about 5 weeks old, body weight $20\pm1$ g), five in one group. Twenty-four hours after the transplantation of the tumor, a solution of the BN-183B substance in distilled water for injection was administered intraperitoneally to the mice once a day for three successive days. The percent increase in life span (i.e., ILS) was measured by comparing the average number of days of survival of each treated group with that of a control group to which the BN-183B substance was not administered. The results are shown in Table 3.

TABLE 3

| Dose per Administration (mg/kg) | Percent Increase in Life Span (%) | |
| --- | --- | --- |
| | P-388 | L-1210 |
| 4 | 66.0 | 59.5 |
| 2 | 79.2 | 45.9 |
| 1 | 54.7 | 32.4 |
| 0.5 | 41.5 | 35.1 |
| 0.25 | 32.1 | 10.8 |

The BN-183B substance further has antiviral activity, and is useful as an antiviral agent. Its antiviral activity was measured by a tissue culture test, and the results are shown in Table 4. It shows a very strong activity against DNA-type and RNA-type viruses. By animal experiments using mice, its anti-Herpes virus activity was measured, and the number of days of 50% survival ($ET_{50}$) was measured. The results are shown in Table 5. The testing method was as follows: ICR-SLC mice (male, 4 weeks old, body weight $20\pm0.5$ g) were used in groups each consisting of 10 mice. Herpes simplex virus type II 196 were administered intraperitoneally to mice in an amount of $10^3$ pfu/mouse. Twenty-four hours later, the BN-183B substance or 5-iodo-2'-deoxyuridine (IUDR) as a control was intraperitoneally administered to the mice. The mice were observed for 2 weeks. It is seen from Table 5 that the same effect as in the group to which 100 mg/kg of IUDR was administered was noted in the group to which 1.25 mg/kg of the BN-183B substance was administered.

TABLE 4

| Virus Used | Dose (mcg/m) | Difference of Log $TCID_{50}$/ml from the Control |
| --- | --- | --- |
| Influenza virus A0/PR-8 | 3.9 | 2.50 |
| Newcastle disease virus Miyadera | 3.9 | 6.00 |
| Vaccinia virus Lister | 3.9 | <3.00 |
| Herpes virus type II 196 | 3.9 | 3.83 |
| Infectious pancreatic necrosis (IPN) virus of rainbow trout | 0.5 | 6.801 |
| Infectious hematopoietic necrosis (IHN) virus of rainbow trout | 0.5 | 3.000 |

TABLE 5

| Drug | Dose (mg/kg) | Cumulative Mortality (%) after the Indicated Number of Days from Inoculation of Virus | | | | | | | | | | $ET_{50}$ (days) |
| --- | --- | --- | --- | --- | --- | --- | --- | --- | --- | --- | --- | --- |
| | | 5 | 6 | 7 | 8 | 9 | 10 | 11 | 12 | 13 | 14 | |
| BN-183B | 2.5 | 0 | 10 | 20 | 70 | 80 | 100 | | | | | 7.65 |
| " | 1.25 | 0 | 20 | 20 | 60 | 70 | 70 | 80 | 90 | 90 | 90 | 8.38 |
| IUDR | 100 | 0 | 0 | 30 | 40 | 60 | 70 | 70 | 70 | 70 | 70 | 8.50 |
| No drug was administered | | 0 | 10 | 40 | 90 | 100 | | | | | | 7.61 |

As regards the novelty of the present substance BN-183B having the aforesaid physicochemical and bacteriological characteristics, we have examined Japanese Patent Applications (OPI), Japanese Patent Publications, the Japanese language publication *Antibiotics,* Volumes 1 and 2 and Supplements I and II (written by Yusuke Sumiki), Index of Antibiotics from Actinomycetes (written by Hamao Umezawa) and Chemical Abstracts. No substance corresponding to the BN-183B substance has been located.

The following Examples illustrate the present invention. It is obvious, however, that many modifications or modifying means not illustrated in these examples can be used in this invention without departing from the spirit and scope of the invention.

EXAMPLE 1

15 liters of a culture medium containing 1.5% of glycerol, 1% of dextrin, 2% of defatted soybean meal, 0.5% of potassium chloride, 0.2% of calcium carbonate and 0.03% of a silicone oil as an anti-foamer was charged into a 30-liter fermentation tank, sterilized at 120° C. for 10 minutes, and cooled. Seeds of Pseudomonas sp. BN-183 (FERM-P No. 3332) pre-cultivated for 2 days in the same medium as described above in two Sakaguchi flasks were aseptically inoculated into the fermentation tank. The seeded culture was cultivated with stirring and aeration at 28° C. (the flow rate of air 15 l/min; the stirring speed 200 rpm). After cultivation for 2 days, 13 liters of a culture broth (130 mcg/ml) was obtained. To the culture broth was added 40 g of an activated carbon for chromatographic use (a product of Wako Purechemical Industries, Ltd.) and the mixture was stirred, after which the activated carbon was separated by decantation. The activated carbon was packed into a column. The column was washed with 1 liter of 50% aqueous solution of acetone, and eluted with an 80% aqueous solution of acetone having a pH of 2 to obtain active fractions. The acetone in the active fractions was distilled off under reduced pressure, and the residue was charged to a column of 300 ml of CM Sephadex C-25 (a product of Pharmacia Co., Sweden) to cause an active ingredient to be adsorbed to it. The Sephadex column was washed with water, and eluted with 0.1 M sodium chloride aqueous solution to obtain active fractions. The active fractions were charged to a column (150 ml) of Diaion HP-20 (a trade name, a product of Mitsubishi Chemical Industries, Ltd., Japan) to cause adsorption of an active ingredient. The column was washed with water to remove sodium salt, and then an active ingredient was eluted with 80% aqueous methanol solution. The active fractions were concentrated to dryness under reduced pressure to obtain 230 mg of BN-183B substance as a yellow powder having a purity of about 70%.

EXAMPLE 2

350 liters of a cultivation medium containing 2% of glycerol, 1% of dextrin, 3% of defatted soybean meal, 0.5% of potassium chloride, 0.3% of calcium carbonate and 0.03% of a silicone oil as an anti-foamer was charged into a 570-liter fermentation tank, sterilized at 120° C. for 20 minutes, and cooled. 20 liters of seeds of Pseudomonas sp. BN-183 (FERM-P No. 3332) pre-cultivated for 24 hours in the same fermentation tank as in Example 1 were aseptically inoculated into the fermentation tank. The seeded culture was cultivated with stirring and aeration at 28° C. for 2 days (the air flow rate 200 l/min; the stirring speed 100 rpm) to obtain 320 liters of a culture broth (200 mcg/ml). The solids were removed by filtration, and 300 liters of a filtrate was obtained.

To the filtrate was added 30 liters of Diaion HP-20, and the mixture was stirred to cause an active ingredient to be adsorbed on the resin. The resin was washed with 60 liters of a 50% aqueous solution of methanol, and eluted three times with 60 liters of an 80% aqueous solution of methanol to obtain an active ingredient. Methanol was distilled off under reduced pressure, and the aqueous solution was diluted to 50 liters with water. The diluted aqueous solution was charged to a 9-liter column of CM Sephadex C-25 previously swollen with water thereby to cause adsorption of an active ingredient. The column was washed with 12 liters of water, and eluted with a 0.1 M aqueous solution of sodium chloride. The active fractions (16 liters) were charged to a 10-liter column of Diaion HP-20 to cause the adsorption of an active ingredient. The resin was washed with water to remove the sodium chloride and then eluted with a 50% aqueous solution of methanol. The active fractions were concentrated under reduced pressure to afford 8.3 g of BN-183B substance as a yellow powder having a purity of about 90%.

The powder was dissolved in 300 ml of methanol. The insoluble matter was removed, and the solution was passed through a column of 200 ml of activated carbon filled with methanol, and developed with methanol. The active fractions were concentrated to dryness under reduced pressure to afford 6.7 g of BN-183B substance as a pure product.

While the invention has been described in detail and with reference to specific embodiments thereof, it will be apparent to one skilled in the art that various changes and modifications can be made therein without departing from the spirit and scope thereof.

What is claimed is:

1. An antibiotic designated BN-183B substance whose hydrochloride has the following characteristics or a pharmaceutically acceptable salt thereof
   (1) Elemental analysis values: C 39.84%, H 5.25%, N 6.43%, Cl 22.90%
   (2) Molecular weight: 383
   (3) Molecular formula: $C_{14}H_{20}N_2O_6Cl_2 \cdot HCl$
   (4) Melting point: begins to turn brownish at 190° C. and to foam and decompose at 214° C.
   (5) Ultraviolet absorption spectrum: shown in FIG. 1
   (6) Infrared absorption spectrum: Absorption bands at 3400, 3020, 1680, 1620, 1570, 1520, 1400, 1360, 1330, 1270, 1240, 1180, 1160, 1130, 1090, 1080, 1020, 930, 880, 850, 830, 800, 740, 700 $cm^{-1}$ and absorption spectrum as shown in FIG. 2.
   (7) Specific rotation: $[\alpha]_D^{23}$ $-9°$ (c=1, water)
   (8) Solubility: very soluble in water, slightly soluble in methanol, and scarcely soluble in acetone, chloroform and ethyl acetate
   (9) Color reactions:
      Positive: ferric chloride, ninhydrin and Fehling
      Negative: Molish and biuret
   (10) Distinction by neutrality, acidity and basicity: behaves as a basic substance in filter paper electrophoresis
   (11) Appearance: white to slightly yellowish powder
   (12) Rf values in thin-layer chromatography:
      Butanol-acetic acid-water (2:2:1): 0.66
      Ethyl acetate-acetic acid-water (60:17:17): 0.34
      Butanol-pyridine-acetic acid-water (6:4:1:3): 0.65.

2. A pharmaceutical preparation which comprises an antibiotically effective amount of the BN-183B substance or the pharmaceutically acceptable salt thereof of claim 1 as an active ingredient and a pharmaceutically acceptable carrier or diluent.

* * * * *